US010034494B2

United States Patent
Ampolini et al.

(10) Patent No.: US 10,034,494 B2
(45) Date of Patent: Jul. 31, 2018

(54) RESERVOIR FOR AEROSOL DELIVERY DEVICES

(71) Applicant: RAI Strategic Holdings, Inc., Winston-Salem, NC (US)

(72) Inventors: Frederic Ampolini, Winston-Salem, NC (US); Frank S. Silveira, Wilmington, MA (US); John DePiano, Burlington, MA (US); Craig Demarest, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 197 days.

(21) Appl. No.: 14/854,968

(22) Filed: Sep. 15, 2015

(65) Prior Publication Data

US 2017/0071249 A1  Mar. 16, 2017

(51) Int. Cl.
| | |
|---|---|
| *A24F 47/00* | (2006.01) |
| *H05B 1/02* | (2006.01) |
| *H05B 3/00* | (2006.01) |
| *A61M 15/06* | (2006.01) |
| *A61M 11/04* | (2006.01) |

(52) U.S. Cl.
CPC ......... *A24F 47/008* (2013.01); *A61M 11/042* (2014.02); *A61M 15/06* (2013.01); *H05B 1/0297* (2013.01); *H05B 3/0014* (2013.01)

(58) Field of Classification Search
CPC .............................. A24F 47/008; A24F 47/00
USPC .......................................................... 131/329
See application file for complete search history.

(56) References Cited

U.S. PATENT DOCUMENTS

| | | | |
|---|---|---|---|
| 4,945,931 | A | 8/1990 | Gori |
| 5,019,122 | A | 5/1991 | Clearman et al. |
| 5,894,841 | A | 4/1999 | Voges |
| 7,972,254 | B2 | 7/2011 | Stokes et al. |
| 8,042,550 | B2 | 10/2011 | Urtsev et al. |
| 8,459,271 | B2 | 6/2013 | Inagaki |
| 8,470,215 | B2 | 6/2013 | Zhang |
| 8,695,609 | B2 | 4/2014 | Dube et al. |
| 8,739,802 | B2 | 6/2014 | Fagg |

(Continued)

FOREIGN PATENT DOCUMENTS

| | | | | |
|---|---|---|---|---|
| CN | 104095291 A | | 10/2014 | |
| WO | WO 2015/077645 A1 | | 5/2015 | |
| WO | WO 2015077645 A1 | * | 5/2015 | ........... A24F 47/008 |

OTHER PUBLICATIONS

International Search Report and Written Opinion of the International Searching Authority dated Feb. 9, 2017 for PCT Application No. PCT/US2016/051638 (15 pp.).

*Primary Examiner* — Abdullah Riyami
*Assistant Examiner* — Nader Alhawamdeh
(74) *Attorney, Agent, or Firm* — Brinks Gilson & Lione

(57) ABSTRACT

An aerosol delivery device or electronic cigarette generates an aerosol or vapor for consumption by a consumer. The device may include a cartridge holding an aerosol precursor substance or fluid that is turned into the aerosol or vapor. The fluid may be stored in reservoir that allows for the fluid to be passed to an atomizer for generating the aerosol. The reservoir may be a flexible bladder that equalizes pressure inside the cartridge to reduce leakage, such as with an internal valve to activate fluid transfer. Alternatively, the reservoir may include one or more capsules that can be broken or melted to release the fluid.

25 Claims, 13 Drawing Sheets

(56) References Cited

U.S. PATENT DOCUMENTS

| | | |
|---|---|---|
| 8,820,331 B2 | 9/2014 | Hartmann et al. |
| 8,881,737 B2 | 11/2014 | Collett et al. |
| 9,220,302 B2 * | 12/2015 | DePiano ............... A24F 47/008 |
| 9,597,466 B2 * | 3/2017 | Henry, Jr. ............. A61M 15/06 |
| 9,609,893 B2 * | 4/2017 | Novak, III ............ A24F 47/008 |
| 9,717,276 B2 * | 8/2017 | Brammer ............... A24F 47/008 |
| 2011/0232654 A1 * | 9/2011 | Mass .................... A61M 15/06 |
| | | 131/273 |
| 2012/0285475 A1 | 11/2012 | Liu |
| 2013/0085052 A1 | 4/2013 | Novak, III et al. |
| 2013/0192619 A1 * | 8/2013 | Tucker .................. H01C 17/00 |
| | | 131/329 |
| 2014/0026887 A1 | 1/2014 | Portney |
| 2014/0096782 A1 * | 4/2014 | Ampolini .............. A24F 47/008 |
| | | 131/328 |
| 2014/0261486 A1 | 9/2014 | Potter et al. |
| 2014/0261495 A1 * | 9/2014 | Novak, III ............ A24F 47/008 |
| | | 131/329 |
| 2015/0059780 A1 | 3/2015 | Davis et al. |
| 2015/0117841 A1 | 4/2015 | Brammer et al. |
| 2015/0136158 A1 | 5/2015 | Stevens et al. |
| 2015/0201674 A1 | 7/2015 | Dooly et al. |
| 2015/0216232 A1 | 8/2015 | Bless et al. |
| 2015/0230521 A1 | 8/2015 | Talon |
| 2015/0245659 A1 * | 9/2015 | DePiano ............... A24F 47/008 |
| | | 392/397 |
| 2015/0351456 A1 * | 12/2015 | Johnson ................ A24F 47/008 |
| | | 131/329 |
| 2017/0071249 A1 * | 3/2017 | Ampolini ............. A24F 47/008 |

\* cited by examiner

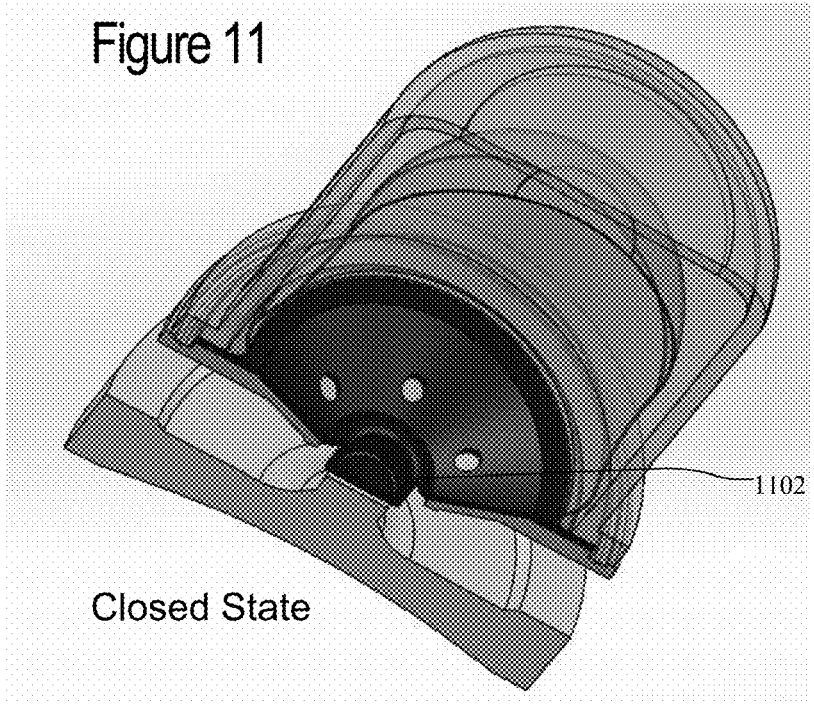
Figure 11 — Closed State
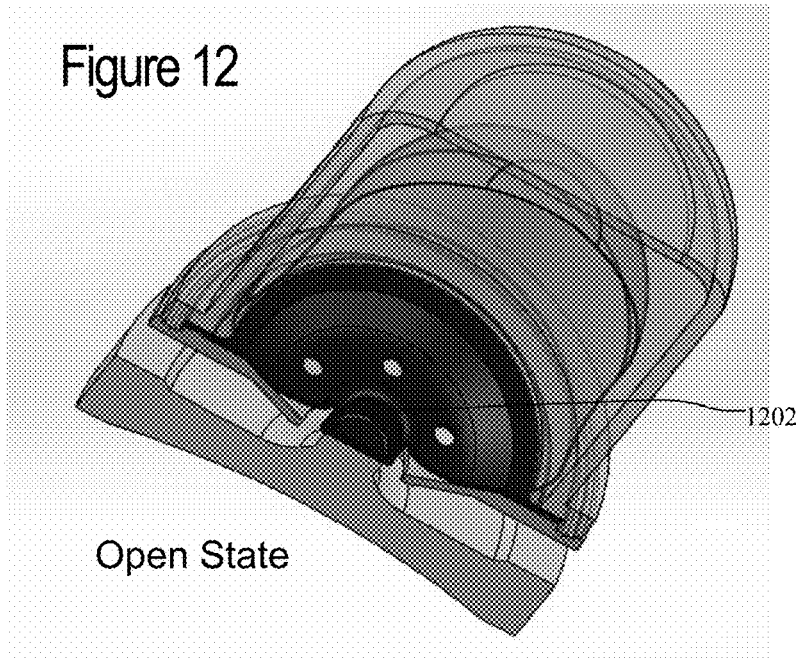
Figure 12 — Open State

Elastomeric displaces and open fluid path

Sealed State

Open State

Breaking Mechanism for the Capsule(s)

RESERVOIR FOR AEROSOL DELIVERY DEVICES

TECHNICAL FIELD

The present disclosure relates to aerosol delivery devices such as personal vapor inhaling units, vaporizers, or smoking articles that may utilize electrically generated heat for the production of aerosol (e.g., smoking articles commonly referred to as electronic cigarettes). The smoking articles or vaporizers may be configured to heat an aerosol precursor substance (such as a formulation incorporating glycerin and nicotine) to form the aerosol for inhalation. This disclosure relates to a system and method for using a collapsible bladder or breakable capsule(s) that hold or contain the aerosol precursor. Of particular interest are products made or derived from tobacco, or that otherwise incorporate tobacco, and that are intended for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al; which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, other types of smoking articles have been proposed in U.S. Pat. No. 5,505,214 to Collins et al.; U.S. Pat. No. 5,894,841 to Voges; U.S. Pat. No. 6,772,756 to Shayan; and U.S. Pat. App. Pub. Nos. 2006/0196518 to Hon; 2007/0267031 to Hon; 2014/0261495 to Novak III et al. and 2015/0230521 to Talon; which are incorporated herein by reference.

It would be desirable to provide an aerosol delivery device (such as an aerosol delivery smoking system commonly referred to as an electronic cigarette) that is capable of providing aerosol in the form of a vaporized substance in a consistent and pleasing manner. Thus, it would be desirable to provide an aerosol delivery device that has components or features that assist in regulating of amount of aerosol precursor available for vaporization, and hence controlling the amount of aerosol precursor available for vaporization and aerosol formation for inhalation.

SUMMARY

The present disclosure relates to aerosol delivery devices, methods of forming such devices, and elements of such devices. The aerosol delivery devices can provide for more consistent distribution of the aerosol precursor substance. When the amount of the aerosol precursor substance (i.e. liquid or e-liquid) is consistent, the smoking (i.e. vaping) experience may be most pleasing to the user. Consistency may be achieved by controlling the amount of liquid that is vaporized. However, the amount of liquid that is vaporized may vary as the volume of the liquid in the device changes. The fluid reservoir in the cartridge may have leakage caused by pressure or temperature changes which result in inconsistent control of the amount of liquid that is vaporized. Utilization of a flexible bladder or capsule may help to regulate and control the flow of the liquid.

In one embodiment, a cartridge assembly for an aerosol delivery device includes a flexible bladder that stores an aerosol precursor substance and a supporting tube that holds the flexible bladder. The assembly includes a plug at one end of the supporting tube that seals the flexible bladder to control leakage except for a porous portion of the plug that allows the aerosol precursor substance through.

In another embodiment, an electronic cigarette includes a battery portion and a cartridge that receives power from the battery portion and stores a fluid that is vaporized. The cartridge includes a flexible bladder holding the fluid, a tube supporting the flexible bladder, and a cap that seals the flexible bladder, wherein the cap includes a porous material for transporting the fluid from the bladder.

In another embodiment, vaporization device includes a mouthpiece for receiving air with vapor and a soft fluid bladder that stores a fluid and reduces excessive air by collapsing as the fluid is removed. The device includes support cylinder that supports the soft fluid bladder and a porous material cap that is disposed on one end of the support cylinder and coupled with the soft fluid bladder for leaking a controlled amount of the fluid. The device further includes an atomizer that generates the vapor from the fluid stored in the soft fluid bladder.

In another embodiment, an aerosol delivery device includes one or more capsules containing an aerosol precursor substance. A mechanism releases the aerosol precursor substance. The mechanism may cause a breaking or heating of the capsules. A vaporizer receives the aerosol precursor substance after the releasing and generates an aerosol by vaporizing the aerosol precursor substance.

BRIEF DESCRIPTION OF THE DRAWINGS

Figure 1:
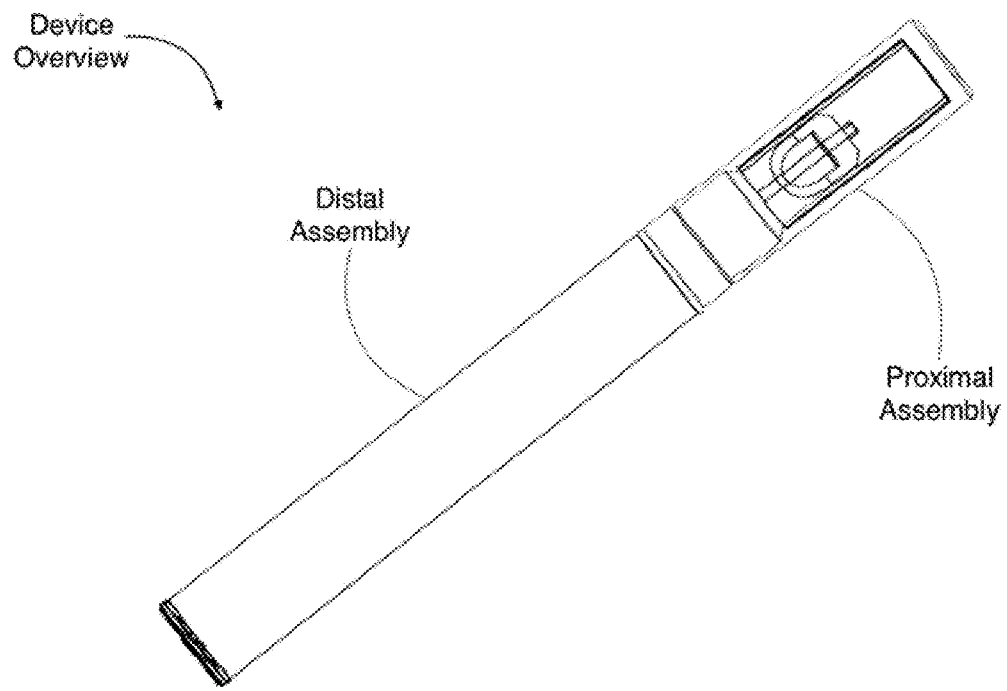

Having thus described the disclosure in the foregoing general terms, reference will now be made to the accompanying drawings, which are not necessarily drawn to scale, and wherein:

FIG. 1 illustrates an aerosol delivery device in a two piece assembly implementation.

Figure 2:
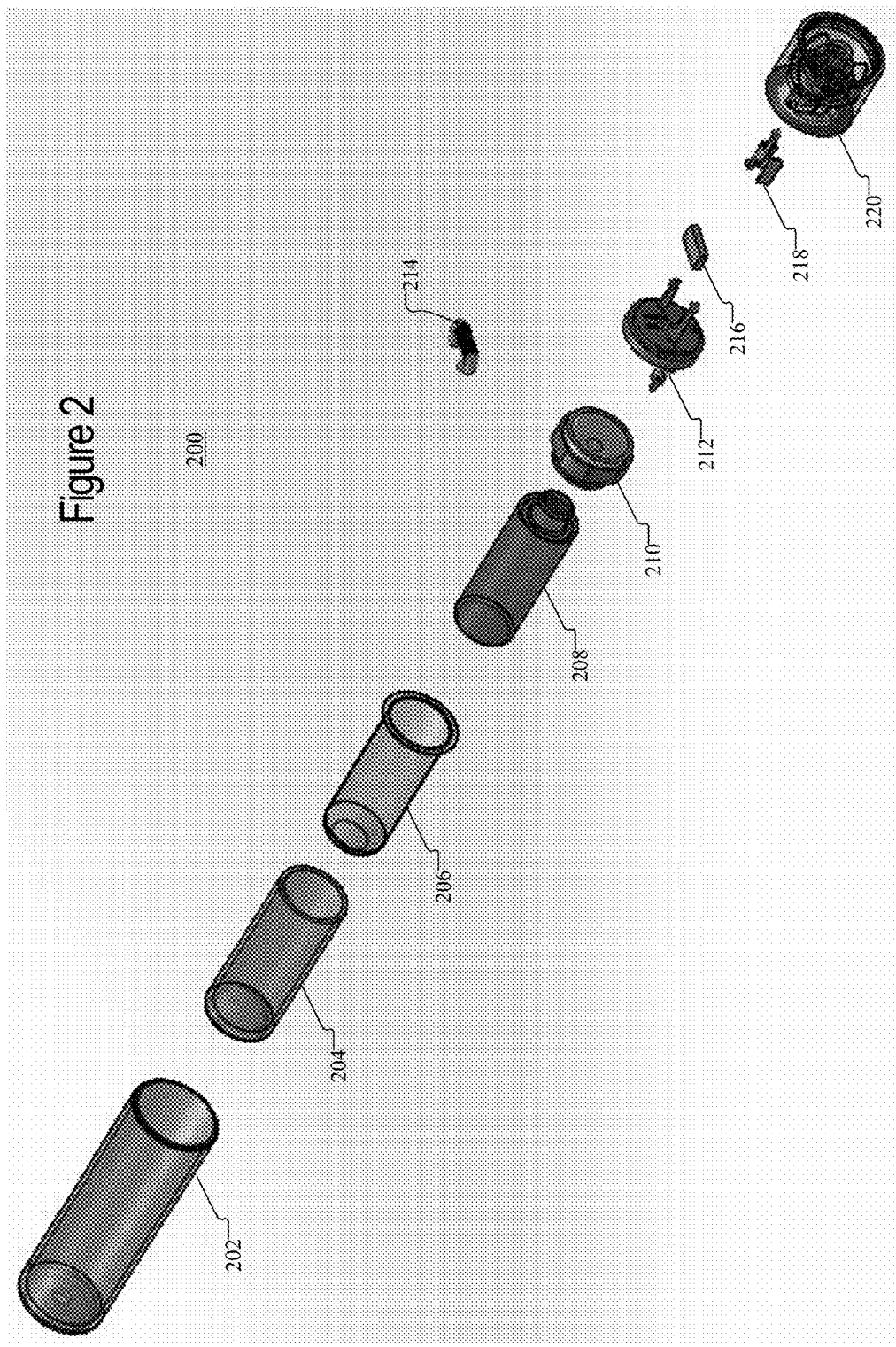

FIG. 2 illustrates a cartridge for an aerosol delivery device including a bladder portion.

Figure 3:
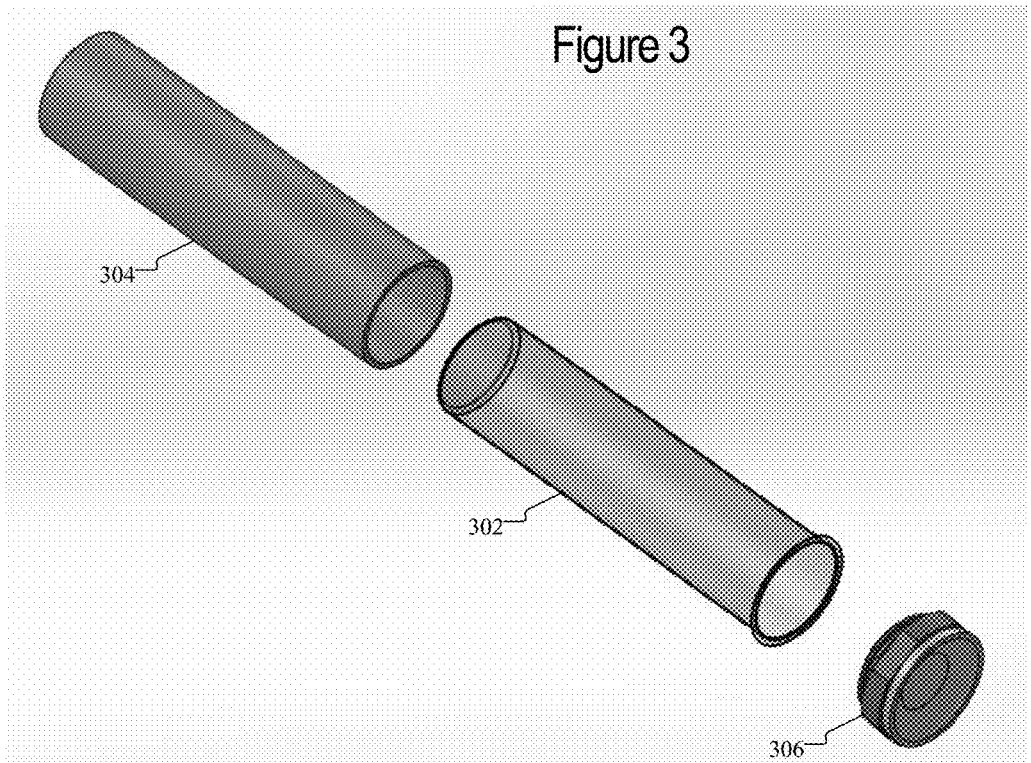

FIG. 3 illustrates a fluid container for a cartridge in an aerosol delivery device.

Figure 4:
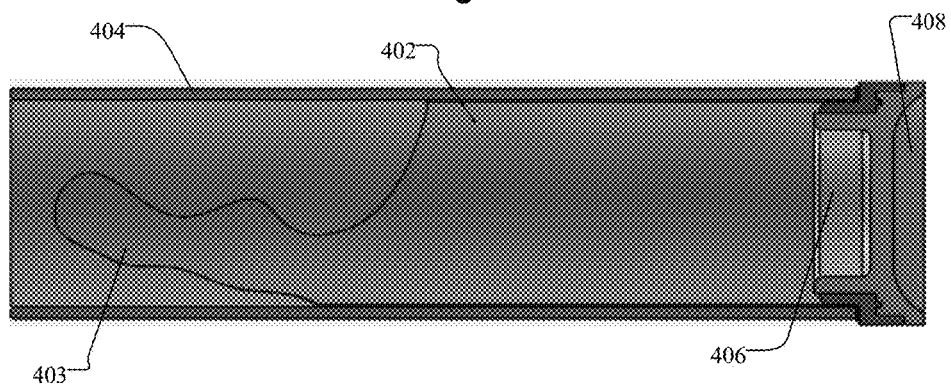

FIG. 4 illustrates the fluid container of FIG. 3 in a closed state.

Figure 5:
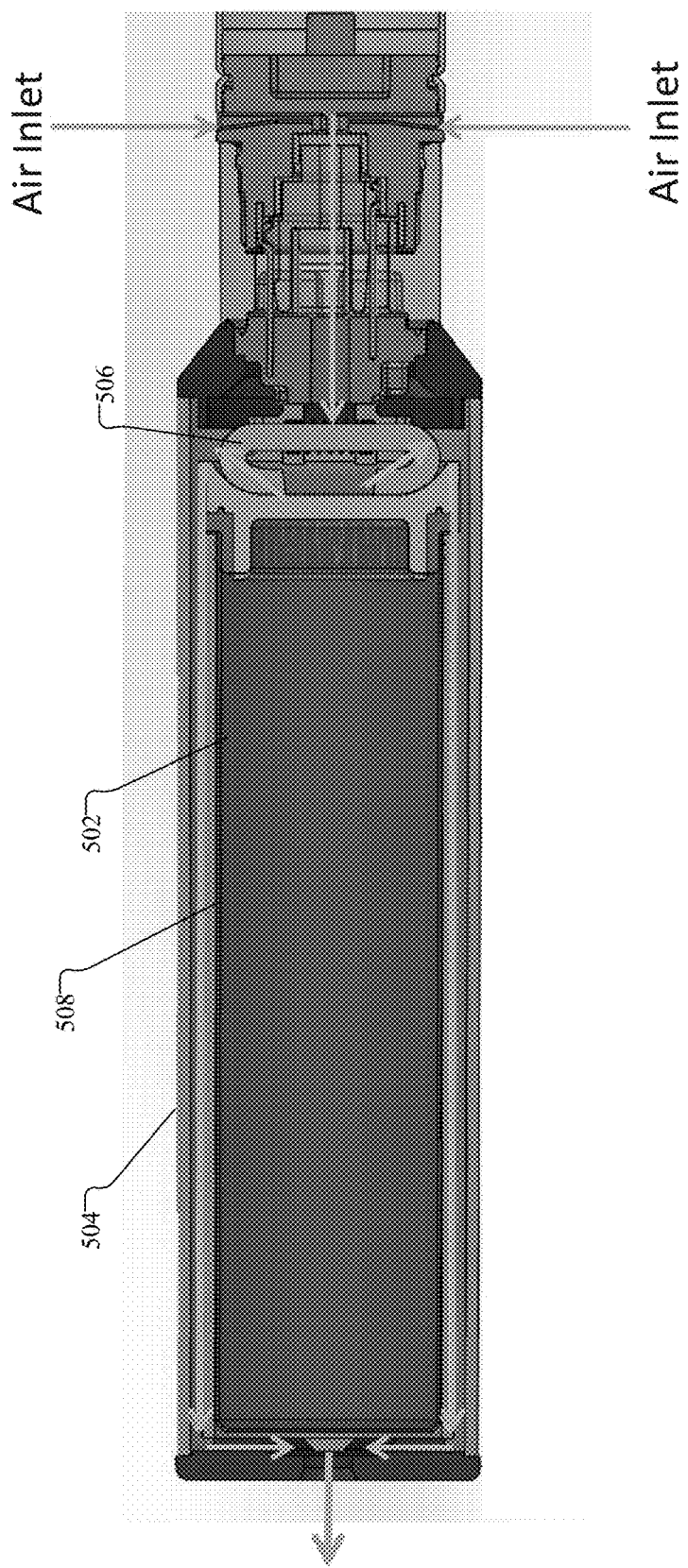

FIG. 5 illustrates air flow in the cartridge.

Figure 6:
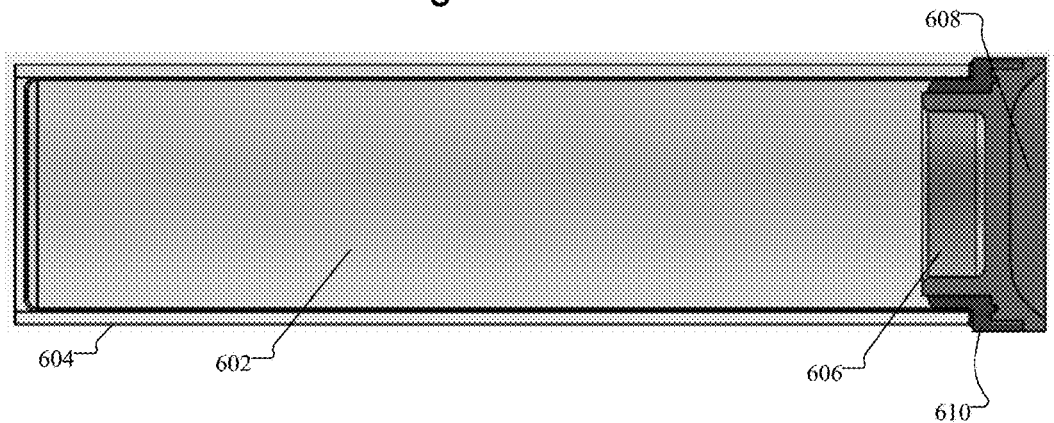

FIG. 6 illustrates a sealed bladder in a cartridge for an aerosol delivery device.

Figure 7:
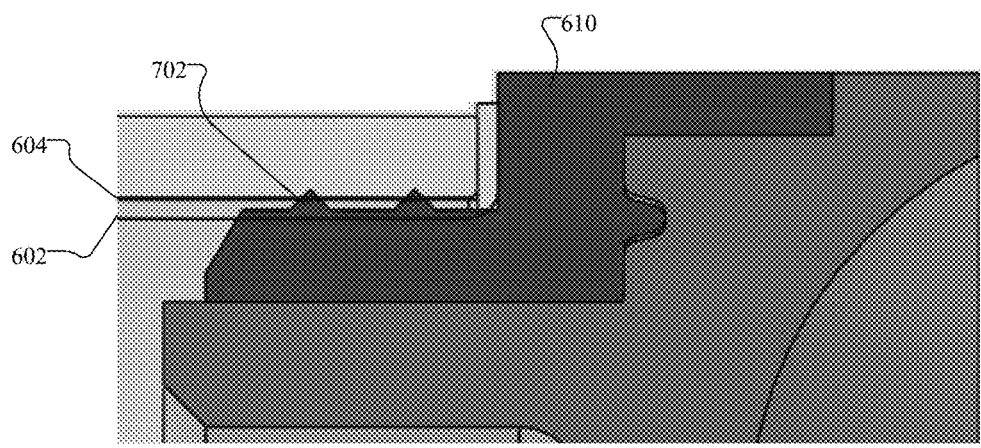

FIG. 7 illustrates one embodiment of a sealing mechanism for sealing a bladder in a cartridge.

Figure 8:
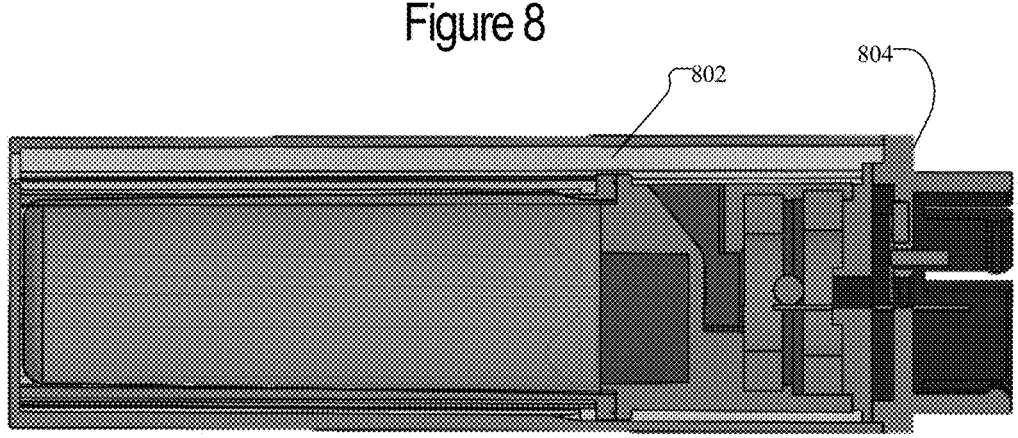

FIG. 8 illustrates an embodiment of a cartridge with a modified air path.

Figure 9:
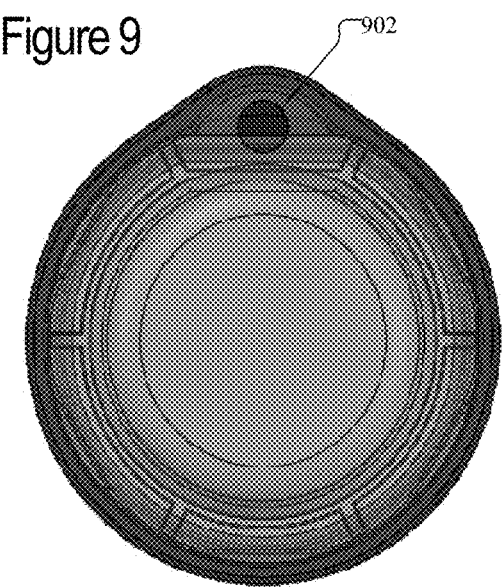

FIG. 9 illustrates an embodiment of an end of the cartridge in FIG. 8 with the modified air path.

Figure 10:
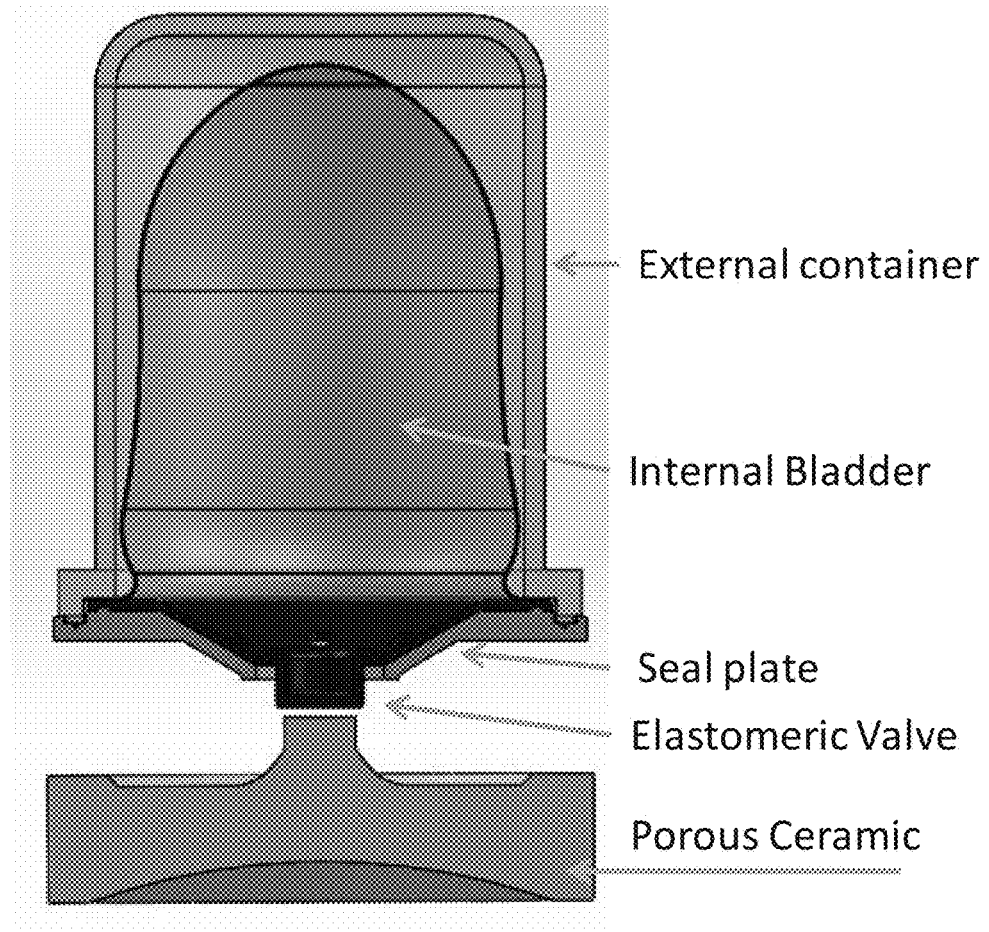

FIG. 10 illustrates a cartridge with a valve connection.

FIG. 11 illustrates a closed state of the elastomeric valve shown in FIG. 10.

FIG. 12 illustrates an open state of the elastomeric valve shown in FIG. 10.

Figure 13:
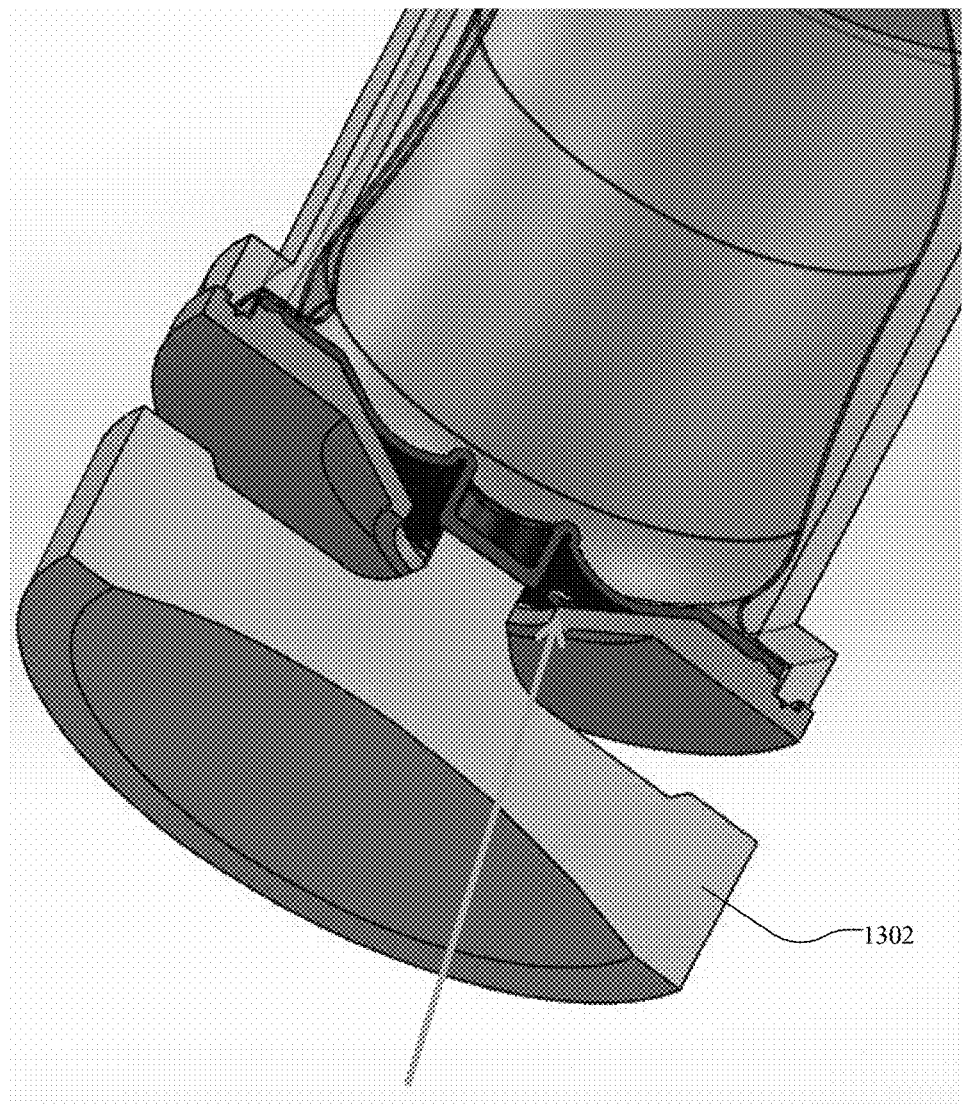

FIG. 13 illustrates another elastomeric valve.

Figure 14:
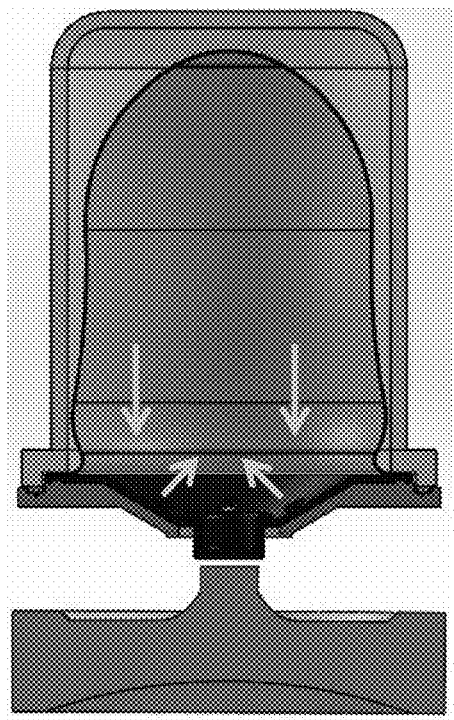

FIG. 14 illustrates a sealed state of the cartridge.

Figure 15:
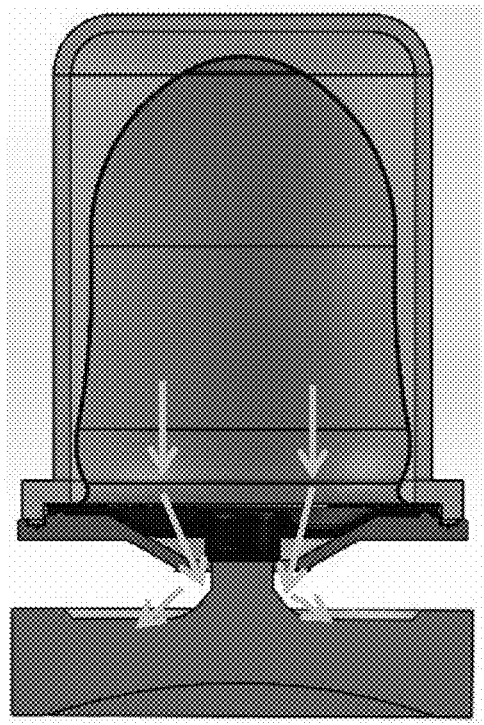

FIG. 15 illustrates an open state of the cartridge.

Figure 16:
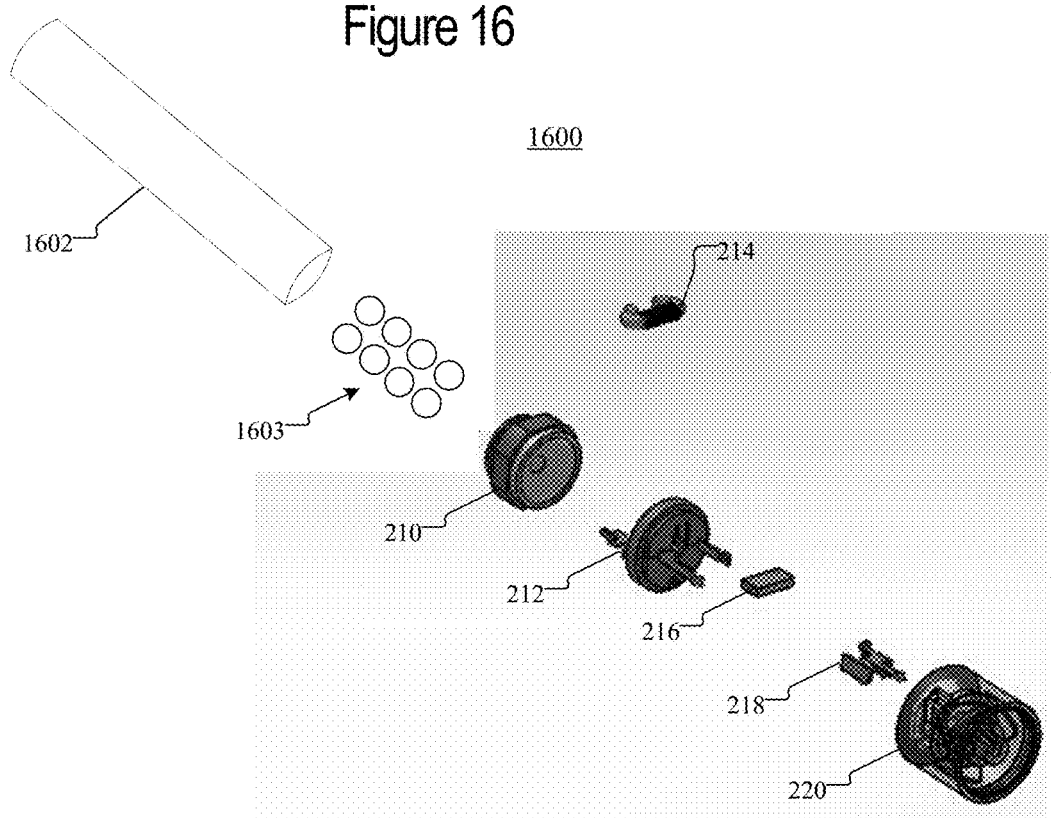

FIG. 16 illustrates a cartridge for an aerosol delivery device including one or capsules.

Figure 17:
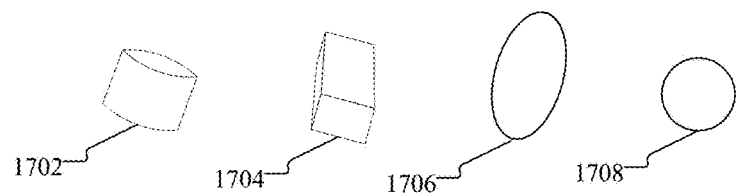

FIG. 17 illustrates an alternative embodiment of capsules.

Figure 18:
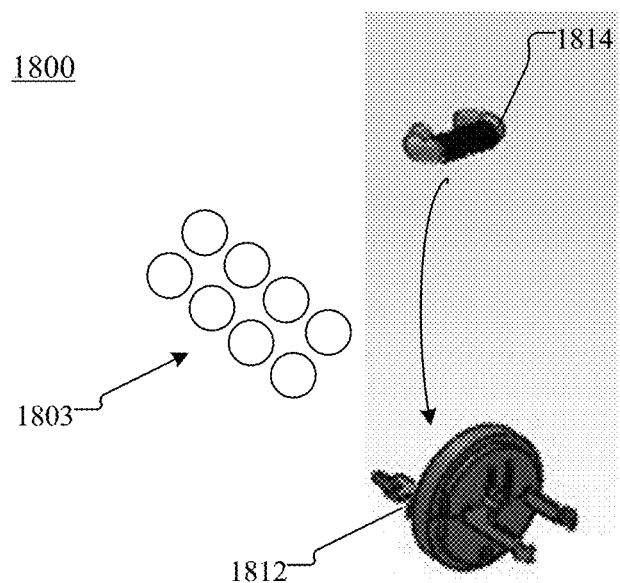

FIG. 18 illustrates an alternative cartridge for an aerosol delivery device including one or capsules disposed adjacent the heating element.

Figure 19:
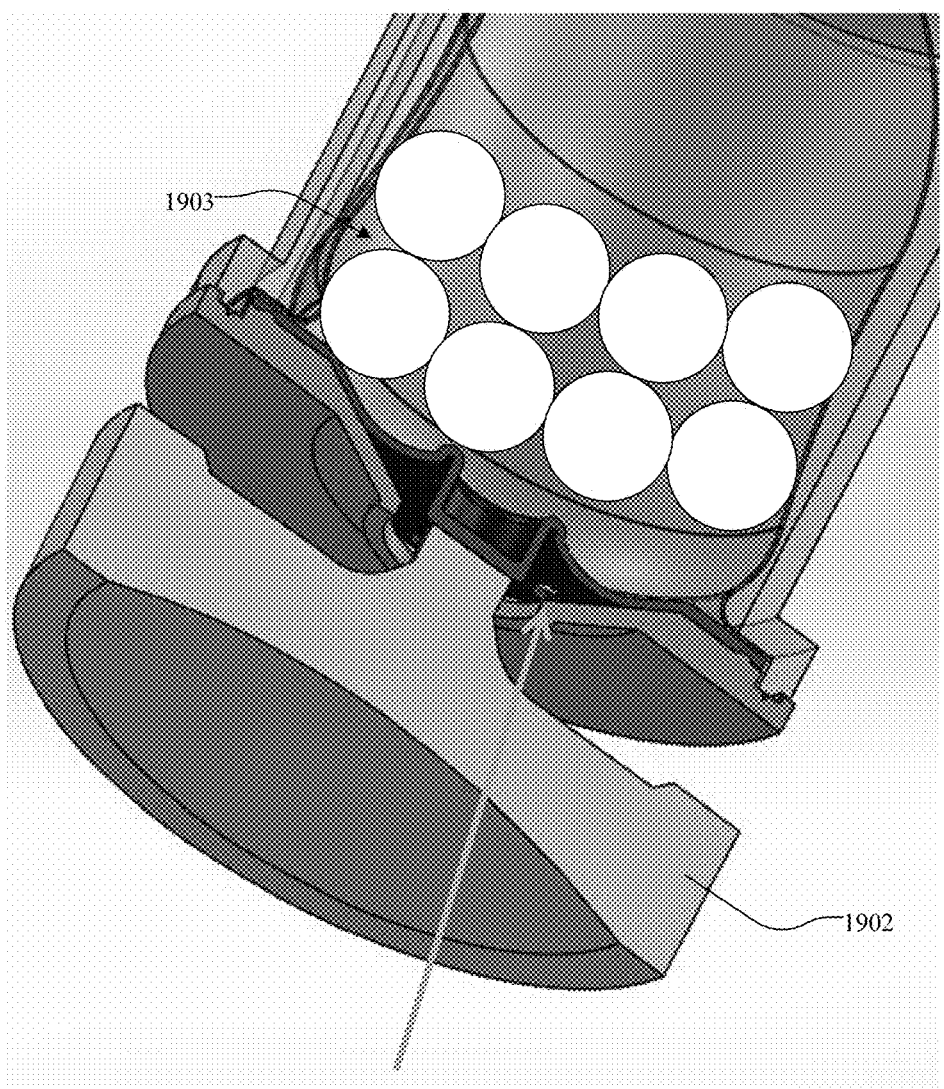

FIG. 19 illustrates a breaking mechanism for the capsules.

DESCRIPTION OF THE EMBODIMENTS

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. As used herein, an aerosol delivery system may include an electronic cigarette ("e-Cig") or a personal vaporizing unit ("PVU") that uses electrical energy to heat a material to form an inhalable substance. Unlike regular cigarettes, the byproduct generated by these devices is not a smoke, but rather an aerosol or a vapor resulting from the volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. For some aerosol delivery devices, an elongated body resembling the shape of a cigarette or cigar can be a formed from a single, unitary housing, or the elongated housing can be formed of two or more separable bodies. For example, an aerosol delivery device can comprise an elongated shell or body that can be substantially tubular in shape and, as such, resemble the shape of a conventional cigarette or cigar. In one implementation, all of the components of the aerosol delivery device are contained within a single housing. Alternatively, an aerosol delivery device can comprise two or more housings that are joined and are separable. For example, an aerosol delivery device can possess at one end a control body comprising a housing containing one or more reusable components (e.g., a rechargeable battery and various electronics for controlling the operation of that article), and at the other end and removably attached thereto an outer body or shell containing a portion including one or more aerosol precursor components, such as flavors and aerosol formers. In various implementations, this portion may be a disposable portion (e.g., a disposable cartridge) or a refillable portion (e.g., a refillable tank).

Embodiments of this application include a non-rigid tank with a flexible bladder for equalizing pressure and reducing leakage. In contrast with a more rigid tank, the flexible bladder is the ability to keep air out of the reservoir or vessel. If there were air in the vessel, heating/cooling or increases/decreases in pressure (which may be caused by expansion in the air volume) are avoided as the bladder is free to expand or contract. A rigid vessel may experiences a pressure differential between inside and outside the rigid tank, either forcing liquid and/or air out, or taking in air while it equalizes. The flexible bladder may prevent air from entering even when the fluid in the bladder is removed. The bag may be in a collapsed or deflated state. With a flexible bladder, the cartridge may be disposable.

Aerosol delivery devices of the present disclosure can be formed of an outer housing or shell that is not substantially tubular in shape but may be formed to substantially greater dimensions. The housing or shell can be configured to include a mouthpiece and/or may be configured to receive a separate shell (e.g., a cartridge, a tank) that can include consumable elements, such as a liquid aerosol former, and can include a vaporizer.

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow from the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouth end region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

FIG. 1 illustrates an aerosol delivery device in a two piece assembly implementation. In the exemplary two piece assembly, there is a distal end (distal assembly) and a proximal end (proximal assembly). The distal assembly may be referred to as a control body and may include the battery and microprocessor. The proximal assembly may be referred to as the tank and may include the cartridge (with fluid reservoir) and atomizer. Although not shown, the distal assembly interfaces with the proximal assembly by a connection interface such that energy from a power source such as a battery or capacitor may be transmitted to the proximal assembly. Examples of batteries that can be used according to the disclosure are described in U.S. Pat. Pub. No. 2010/0028766 to Peckerar et al., the disclosure of which is incorporated herein by reference in its entirety.

The aerosol delivery device may incorporate a sensor or detector for control of supply of electric power to a heater when aerosol generation is desired (e.g., upon draw during use). As such, for example, there is provided a manner or method of turning off the power supply to the heater when the aerosol delivery device is not being drawn upon during use, and for turning on the power supply to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The distal assembly may include a main body that houses a battery or capacitor, one or a plurality of microprocessors, an LED or light at the distal aspect of the device. The distal assembly or battery portion may include a number of electronic components, and in some examples may be formed of an electronic or printed circuit board (PCB) that supports and electrically connects the electronic components. The electronic components may include a microprocessor or processor core, and a memory. In some examples, the control component may include a microcontroller with integrated processor core and memory, and which may further include one or more integrated input/output peripherals. In some examples, the control component may be coupled to a communication interface to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated by reference in its entirety. And examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

The distal assembly may connect with the cartridge connector on the proximal assembly. The proximal assembly may include an atomizer housing which houses a secondary wick and heating element or elements. The atomizer housing may include connections for integrating a microprocessor, the power source, and the heating element. The atomizer housing may also include a wick element that is in contact with the fluid to be vaporized. The fluid to be vaporized may be stored in a fluid reservoir. The atomizer housing and fluid reservoir may be disposed in a chamber housing, which also functions as the mouthpiece of the PVU.

In some example implementations, the proximal assembly or cartridge may be referred to as being disposable or as being reusable. In another example, the proximal assembly may have a replaceable battery or a rechargeable battery and thus may be combined with any type of recharging technology, including connection to a typical alternating current electrical outlet, connection to a car charger (i.e., a cigarette lighter receptacle), and connection to a computer, such as through a universal serial bus (USB) cable or connector. The proximal assembly may include a tank comprising a refillable reservoir. The reservoir may be configured to retain the aerosol precursor composition (e.g. fluid). The reservoir particularly may be formed of or coupled with a wick made of a porous material (e.g., a fibrous material). As described below with respect to FIG. 2-5, the cartridge may include a bladder for storing the fluid substance.

FIG. 2 illustrates a cartridge 200 for an aerosol delivery device including a bladder portion. The cartridge 200 may include an external tube or mouthpiece 202 and a bladder support cylinder 204 for supporting a liquid container bladder 206. The liquid container bladder 206 may be a reservoir that contains a fluid 208 or e-liquid that is the precursor substance to the aerosol. An aerosol precursor composition may be retained in the bladder 206. Liquid components, for example, can be retained by the bladder 206. The bladder 206 can be in a fluid connection through a plug 210. The plug 210 may cap the bladder 206 to hold the fluid 208. The plug 210 may be a silicone or ceramic material, but other materials may also be used, such as CA. The device shown is comprised of a ceramic center core with a silicone outer case that seals the perimeter from leakage, as the ceramic will let the fluid to migrate through onto the wick 214.

A flow-tube 212 or terminal support may be provided that includes or couples with a heater 214 (sometimes referred to as a heating element). The flow-tube 212 may allow air to flow through it and act as a terminal support element to support the heater 214. The heater 214 shown in FIG. 2 may be a wick that includes a coil wrapped around the wick. The wick receives fluid that is heated by the heater coil. The plug 210 and/or flow-tube 212 may be adapted to wick or otherwise transport a fluid stored in the bladder 206 to the heater 214. As shown, the center ceramic portion of the plug 210 can transport liquid to the wick. The heater 214 may be supported by the flow-tube 212, which acts as an inlet that air passes through.

A valve may be between the bladder 206 and a center ceramic of the plug 210. This may release fluid when the valve is activated. The flow-tube 212 might be used to activate the valve. The valve may be positioned between the fluid reservoir and the heater 214, and configured to control an amount of fluid passed or delivered from the reservoir to the heater. Various examples of materials configured to produce heat when electrical current is applied therethrough may be employed to form the heater 214. The heater in these examples may be resistive heating element such as a coil. Example materials from which the coil may be formed include Kanthal (FeCrAl), Nichrome, Molybdenum disilicide (MoSi2), molybdenum silicide (MoSi), Molybdenum disilicide doped with Aluminum (Mo(Si,Al)2), graphite and graphite-based materials (e.g., carbon-based foams and yarns) and ceramics (e.g., positive or negative temperature coefficient ceramics).

An end portion of the cartridge 200 may include a smart chip 216, a communication terminal 218, and a cartridge base 220. The smart chip 216 may include an integrated circuit, a memory component, a sensor, or the like. The electronic components of the smart chip 216 may be adapted to communicate using the communication terminal 218 with the distal assembly (battery portion) and/or with an external device by wired or wireless means.

In use, when a user draws on the aerosol delivery device, airflow is detected by a flow sensor (not shown), and the heater 214 is activated to vaporize components of the aerosol precursor composition. Drawing upon a mouthpiece 202 of the aerosol delivery device causes ambient air to enter the air intake and the drawn air combines with the formed vapor to form an aerosol. The aerosol is whisked, aspirated or otherwise drawn away from the heater around the bladder support cylinder 204 and out an opening in the mouthpiece 202 of the aerosol delivery device.

As described, the bladder 206 acts as a reservoir for a substance to be vaporized. That substance may be a liquid (i.e. e-liquid) or other fluid and may be referred to as an aerosol precursor composition or vapor precursor composition. The fluid may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al. and 2014/0060554 to Collett et al., the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Additional representative types of fluids are set forth in U.S. Pat. No. 4,793,365 to Sensabaugh, Jr. et al., U.S. Pat. No. 5,101,839 to Jakob et al., U.S. Pat. No. 6,779,531 to Biggs et al., U.S. Pat. App. Pub. No. 2013/0008457 to Lipowicz et al.; and 2015/0020830 to Koller, as well as WO 2014/182736 to Bowen et al, and Chemical and Biological Studies on New Cigarette Prototypes that Heat Instead of Burn Tobacco, R. J. Reynolds Tobacco Company Monograph (1988), all of which are incorporated herein by reference in their entireties.

The amount of fluid that is incorporated within the aerosol delivery system is such that the aerosol generating piece provides acceptable sensory and desirable performance characteristics. For example, it may be preferred that sufficient amounts of fluid (e.g., glycerin and/or propylene glycol), be employed in order to provide for the generation of a visible mainstream aerosol that in many regards resembles the appearance of tobacco smoke. The amount of fluid within the aerosol generating system may be dependent upon factors such as the number of puffs desired per aerosol generating piece. Typically, the amount of fluid incorporated within the aerosol delivery system, and particularly within the aerosol generating piece, is less than about 2 g, generally less than about 1.5 g, often less than about 1 g and frequently less than about 0.5 g. The flexible bladder 206 (and supporting components) may be re-sized in different embodiments for an optimal amount of fluid.

FIG. 3 illustrates a fluid container for a cartridge in an aerosol delivery device. The fluid container in FIG. 3 may be similar to the fluid container illustrated in FIG. 2. In particular, a flexible bladder 302 may be the same as or similar to the bladder 206 shown in FIG. 2. Likewise, a cap portion 306 may be the same as or similar to the cap 210 shown in FIG. 2. Finally, the tube 304 may be either the external tube 202 or bladder support cylinder 204 shown in FIG. 2.

The flexible bladder 302 may be a flexible bag or similar material. In one embodiment, the bladder 302 may be a latex material or a thin plastic. The flexibility of the bladder 302 may allow for pressure changes or temperature changes that would otherwise disrupt a sealed tank (i.e. non-flexible container), such as leakage. In particular, the flexible bladder 302 may equalize the pressure exterior to the reservoir and the inside pressure of the reservoir. The bladder 302 can adapt and adjusts for any pressure changes.

The seal of the bladder 302 may be a porous membrane within the cap 306. In other words, the cap 306 may form an elastomeric seal on the open end of the bladder. The tube 304 may be open-ended for allowing for expansion/contraction of the bladder 302. The cap 306 may be referred to as a plug or seal and provide a means for controlling and generating fluid flow from the bladder 302 to the heating element. Ceramic may be used for the cap 306 because it can be porous enough to allow a light fluid flow to a wick with the heating element. In particular, a silica wick may be in contact with a ceramic (or other porous material) in the cap 306 which receives fluid that is transported to or near the heating element. Other materials other than a ceramic may be utilized with the cap 306 that allow for fluid flow from the bladder 302. For example, cellulose acetate or a porous plastic may be used for the cap 306. The cap 306 may be encased in a silicone boot to prevent leakage except for a desired amount through the porous material of the cap 306.

FIG. 4 illustrates the fluid container of FIG. 3 in a closed state. In particular FIG. 4 illustrates the cap 406 coupled to a tube 404 to seal the bladder 402. The sealing of the bladder 402 prevents leakage of the fluid, but the cap 406 can still allow fluid flow from the bladder through a porous material 408. The porous material 408 may include a ceramic, plastic, or other porous material that weeps fluid from the bladder 402. The fluid may be held in the bladder and the air flow (from a user inhaling described with respect to FIG. 5) may trigger fluid flow from the bladder 302. The sealing of the bladder is further discussed below with respect to FIGS. 6-15. FIG. 4 illustrates the flexible nature of the bladder 402. In particular, the bladder 402 may collapse as fluid is dispensed from the bladder 402. The collapsed portion 403 of the bladder 402 results from the bladder not being as full as fluid is removed. The collapsing of the bladder 402 may serve to maintain a balanced pressure within the device. This pressure mitigation may result in a more consistent and controllable amount of fluid that is dispensed through the porous material 408 by preventing potential leakage that may have been caused by pressure differentials.

FIG. 5 illustrates air flow in the cartridge. There may be air inlets through which external air is received in the device. A wick 506 may include a heating element (e.g. coil) that vaporizes fluid that is absorbed onto the wick. The air flow may pass over or near the wick 506 and the heating element and then pass between the external tube 504 and bladder 502. The external tube 504 may be the external tube 304 and the bladder 502 may be the bladder 302 discussed above. In one embodiment the air path outside of the bladder 502 may be between the external tube 504 and a bladder support cylinder 508. The bladder support cylinder 508 may be used to support the bladder 502 and is sealed with a cap, while the external tube 504 results in an air path between the bladder support cylinder 508 and the external tube 504. As discussed above, the air flow may be generated by a user puffing (inhaling) on the device which results in a suction effect that pulls air through the air inlets.

FIG. 6 illustrates a sealed bladder in a cartridge for an aerosol delivery device. A cap or seal may be used to seal the bladder to prevent leakage, but to allow fluid flow upon device usage. As used herein, the term cap or seal may refer to multiple components include a cap 606 and a porous material 608 shown in FIG. 6. Those elements may be separate or may be combined as a singular cap/seal. The cap 606 may include a porous material 608 that allows from fluid flow from the fluid stored in the bladder 602. The bladder 602 is disposed within an external tube 604 for support. The bladder is sealed off to the external tube 604 with a silicone seal 610. The silicone seal 610 prevents fluid leakage, such that the fluid can only flow through the cap 606 and the porous material 608. Although described as silicone in this embodiment, the seal 610 may be formed of alternative materials that can fill the gap between the bladder connection to prevent fluid flow outside of the porous material 608. The silicone seal 610 is further illustrated in FIG. 7.

FIG. 7 illustrates one embodiment of a sealing mechanism for sealing a bladder in a cartridge. The silicone seal 610 may include ridges 702 for causing a compression or friction fit between the bladder 602 and the external tube 604. The compression fit causes the flexible bladder 602 to be pressed against the external tube 604 to prevent fluid leakage. In alternative embodiments, other seals may be utilized (other than a compression fit), including a screw mechanism, fastening mechanism, or gluing mechanism. The sealing that is used is designed to prevent fluid from the flexible bladder 602 from leaking on the outside portion of external tube 604. Rather, the fluid can only pass through the cap 606 and the porous material 608. Because the bladder 602 is flexible, it may need to be sealed in order to prevent this leakage. In one embodiment, the bladder 602 and the sealing mechanism is designed to be a one-time use or disposable cartridge that can be replaced.

FIG. 8 illustrates an embodiment of a cartridge with a modified air path. As discussed, the air flow around the bladder may include a gap between the bladder support cylinder and the external tube. FIG. 8 illustrates a modified air path 802 that includes additional spacing between the bladder support cylinder and the external tube. By shrinking a connector, there may be a lip 804 that can be used for other components (e.g. ultrasonic).

FIG. 9 illustrates an embodiment of an end of the cartridge in FIG. 8 with the modified air path. In particular, the modified air path 902 is shown from an end of the cartridge. The modified air path 902 may include an opening that allows for increased air flow. This modified air path 902 may be a tube that is external to the bladder and/or the external tube but within an outside housing of the aerosol device.

FIG. 10 illustrates a cartridge with a valve connection. The internal bladder may be held within an external container (e.g. external tube or cylindrical support). There may be a seal plate with an elastomeric valve that connects with a porous material (e.g. porous ceramic) for transporting the fluid during usage of the device. The valve may function to hold in the fluid unless it is activated and it allows liquid to seep into the porous ceramic which may contact a wick with a heating element for the vaporization process.

FIG. 11 illustrates a closed state of the elastomeric valve shown in FIG. 10. The elastomeric valve shown in FIG. 10 may be in a closed state when fully extended out from the bladder. The elastomeric valve is in a steady state 1102 awaiting displacement.

FIG. 12 illustrates an open state of the elastomeric valve shown in FIG. 10. The elastomeric valve shown in FIG. 10 may be in a closed state when pressed upwards towards the bladder. The elastomeric valve is in a depressed state 1202 in which the valve has been opened through displacement. In one embodiment, the user may apply the pressure that depresses the valve as shown in and described with respect to FIG. 13.

FIG. 13 illustrates another elastomeric valve. A user may physically press a portion 1302 (e.g. button) that presses into the valve. The pressure on the valve creates an open fluid path when the elastomeric portion is displaced. The elastomer in the relaxed position would seal the openings. The opening of the valve may be by displacement rather than pressure. In one embodiment, the sealed/closed state may be at manufacture and when the user adds the cartridge to their aerosol delivery device, the pressing of the cartridge into the device may cause the pressure needed to activate the valve and create a fluid path. This activation may be a one-time activation (i.e. when the cartridge is installed) or may be needed prior to each usage. For a disposable cartridge, the flexible bladder can remain in a sealed/closed state (with no leakage) until the cartridge is installed.

FIG. 14 illustrates a sealed state of the cartridge. In particular, the center plunger may activate the release or opening of the elastomeric valve. Further, FIG. 14 illustrates the flow path in a closed state. The cartridge may include the elastomeric valve shown and described with respect to FIGS. 10-13. Fluid flow may be completely blocked in a sealed state. Upon manufacture and prior to usage, the cartridge may be in the sealed state. Upon first usage, a user may depress the valve to trigger the open state shown in FIG. 15. FIG. 15 illustrates the flow path being open. The open state is created when the valve is depressed which opens a fluid flow path from the bladder through the ceramic material. The center plunger may activate the opening of the elastomeric valve. The open state may be referred to as an activated state.

In alternative embodiments, the elastomeric valve may be replaced with another component. For example, there may be other components, such as a membrane, that seals the bladder in a closed state, but upon activation provides fluid flow from the bladder. The activation may include an electronic activation (e.g. press a button) or a physical activation (e.g. user depresses end of the device to touch or displace the membrane).

In an alternative embodiment, the reservoir storing the aerosol precursor substance or the fluid intended for aerosol formation may have the form of at least one capsule or otherwise possess a capsule-type of format and configuration. That is, an aerosol precursor substance can be adapted to have a form so as to segregate, or otherwise create physical separation for, that aerosol precursor. A typical capsule-type configuration is provided by an inner region or core of aerosol precursor components, and an outer region or shell that acts as a wall or barrier structure to define the shape and volume of the inner region; as well as entrap, contain or encapsulate the aerosol precursor, thus providing storage or positioning of aerosol precursor in a manner so that the aerosol precursor is physically separated from other components of the aerosol delivery device into which that capsule is incorporated. If desired, a diluent material may be incorporated within the inner region of the capsule along with the aerosol precursor substance. Representative diluents are set forth in U.S. Pat. No. 8,695,609 to Dube et al.; and 2014/0053855 to Hartman et al., each of which are herein incorporated by reference. Preferably, each capsule is enclosed or sealed in such a way that the aerosol precursor substance does not leak from the capsule or may not be accessible from the capsule, prior to desired conditions of use.

Most preferably, a representative capsule is such that the outer shell or wall has sufficient resiliency and integrity to maintain encapsulation of the inner components during normal conditions or storage and handling; but can be broken to release the encapsulated inner components during conditions of normal use. For example, the capsule can be composed of a shell material so as to have a somewhat rigid exterior, or the capsule can have a somewhat flexible overall consistency. The outer wall or shell material of the capsule may be any of the following materials: proteins, polysaccharides, starches, waxes, fats, natural and synthetic polymers, and resins. Exemplary materials for use in the shell may include gelatin, acacia (gum arabic), polyvinyl acetate, potassium alginate, carob bean gum, potassium citrate, carrageenan, potassium polymetaphosphate, citric acid, potassium tripolyphosphate, dextrin, polyvinyl alcohol, povidone, dimethylpolysiloxane, dimethyl silicone, refined paraffin wax, ethylcellulose, bleached shellac, modified food starch, sodium alginate, guar gum, sodium carboxymethylcellulose, hydroxypropyl cellulose, sodium citrate, hydroxypropylmethylcellulose, sodium ferrocyanide, sodium polyphosphates, locust bean gum, methylcellulose, sodium trimetaphosphate, methyl ethyl cellulose, sodium tripolyphosphate, microcrystalline wax, tannic acid, petroleum wax, terpene resin, tragacanth, polyethylene, xanthan gum, and polyethylene glycol. If desired, the capsule can be over-coated with an outer barrier or seal on the outer region with a coating or moisture barrier. U.S. Pat. Pub. No. 2014/0053855 to Hartman et al. further describes capsule materials and is herein incorporated by reference.

The capsule is opened or activated to release the encapsulated contents. Typically, activation is performed by breaking, crushing, or melting of the capsule; and such activation most preferably is initialized by the user of the aerosol delivery device. For example, the user may either press a button to provide crushing of the capsule, or initiate an electronic signal that can further initiate chemical or physical action upon the capsule. Additionally, inhalation (i.e. when the flow sensor is triggered) may result in a physical crushing of the capsule or production of heat can act to degrade the physical integrity of the capsule wall, and hence release the inner, encapsulated contents of the capsule. The activation may be initialized by the user. For example, the user may either press a button, or inhalation (i.e. when the flow sensor is triggered) may activate the capsule. The initialization may include either a chemical reaction to break down the capsule, heating to break down the capsule, or some other electrical signal that breaks the capsule.

A capsule most preferably is positioned within the aerosol delivery device such that it can be broken when desired, and such that the contents of the capsule can be made available for aerosol production or for the enhancement of aerosol that is produced by the aerosol delivery device. As such, it is highly preferable, that contents released from the capsule are located in in the vicinity of the wicking components or resistance heating element of the aerosol delivery device (e.g., the capsules can be in contact with, or in a location sufficiently close to, the components of the aerosol delivery device that generate heat or exhibit increased temperature during conditions of use. Thus, the contents of the capsule, which include aerosol precursor components, can be subjected to heat generated for aerosol formation, and hence can be vaporized for aerosol formation.

Numerous ways of handling breakable capsules and incorporating those breakable capsules into components of smoking articles and vapor delivery systems have been proposed. For example, various types of capsules suitable for use in smoking articles, smoking article components that incorporate breakable capsules, and equipment and techniques associated with manufacturing those smoking article components, are proposed in U.S. Pat. No. 6,631,722 to MacAdam et al.; U.S. Pat. No. 7,479,098 to Thomas et al.; U.S. Pat. No. 7,833,146 to Deal; U.S. Pat. No. 7,984,719 to Dube et al.; U.S. Pat. No. 7,972,254 to Stokes et al.; U.S. Pat. No. 8,186,359 to Ademe et al.; U.S. Pat. No. 8,262,550 to Barnes et al.; U.S. Pat. No. 8,308,623 to Nelson et al.; U.S. Pat. No. 8,353,810 to Garthaffner et al.; U.S. Pat. No. 8,381,947 to Garthaffner et al.; U.S. Pat. No. 8,459,272 to Karles et al.; U.S. Pat. No. 8,739,802 to Fagg; U.S. Pat. No. 8,905,243 to Dixon et al. and U.S. Pat. No. 9,055,768 to Henley et al.; US Pat. App. Pub. Nos. 2010/0184576 to Prestia et al.; 2011/0053745 to Iliev et al.; 2011/0271968 to Carpenter et al.; to Henley et al. and 2013/0085052 to Novak III, et al.; and U.S. patent application Ser. No. 14/835,962, filed Aug. 26, 2015 to Ademe; which are incorporated herein by reference. Additionally, representative cigarette products that possess filter elements incorporating breakable capsules have been marketed throughout the world under the brandnames such as “Marlboro W-Burst 5,” “Kent iSwitch,” “Kool Boost,” “Camel Lights with Menthol Boost,” “Camel Crush,” “Camel Silver Menthol,” “Camel Filters Menthol,” and “Camel Crush Bold.” Furthermore, representative types of vapor delivery systems that incorporate breakable capsules have been proposed in U.S. Pat. Pub. Nos. 2014/0261486 to Potter and 2015/0059780 to Davis; and U.S. patent application Ser. No. 14/282,768 to Sears et al., filed May 20, 2014; which are incorporated herein by reference.

Exemplary types of capsules, capsule ingredients, capsule configurations and formats, capsule sizes, capsule properties and capsule preparation techniques are set forth in U.S. Pat. No. 5,223,185 to Takei et al.; U.S. Pat. No. 5,387,093 to Takei; U.S. Pat. No. 5,882,680 to Suzuki et al.; U.S. Pat. No. 6,719,933 to Nakamura et al.; U.S. Pat. No. 7,754,239 to Mane; U.S. Pat. No. 6,949,256 to Fonkwe et al.; U.S. Pat. No. 7,984,719 to Dube et al.; U.S. Pat. No. 8,470,215 to Zhang and U.S. Pat. No. 8,695,609 to Dube et. al.; U.S. Pat. App. Pub. Nos. 2004/0224020 to Schoenhard; 2005/0196437 to Bednarz et al.; 2005/0249676 to Scott et al. and 2014/0053855 to Hartmann et al.; and PCT WO 03/009711 to Kim and PCT WO 2014/170947 to Iwatani; which are incorporated herein by reference. Additionally, examples of representative types of capsules and capsule components have been commercially available as “Momints” by Yosha!

Enterprises, Inc. and "Ice Breakers Liquid Ice" from The Hershey Company; and representative types of capsules and capsule components have be incorporated into chewing gum, such as the type of gum marketed under the tradename "Cinnaburst" by Cadbury Adams USA.

Representative encapsulated components can vary. One example of an encapsulated formulation includes propylene glycol, glycerin, nicotine, organic acids and flavoring agents. An example of a suitable capsule is composed of an outer shell that possesses chemical and physical properties sufficient to provide a sealed container of good integrity for the encapsulated components. For example, such a shell can be provided using components comparable to use used to create those capsules used for the production of capsules used in filter elements of cigarettes marketed under the brand name "Camel Crush" by R. J. Reynolds Tobacco Company.

FIG. 16 illustrates a cartridge 1600 for an aerosol delivery device including one or capsules. FIG. 16 is similar to the embodiment shown in FIG. 2, except the fluid container 202 with the flexible bladder 206 is replaced with one or more capsules 1603 in a container 1602. Although eight capsules 1603 are illustrated in FIG. 16, there may be just a single capsule for providing the aerosol precursor substance or there may be many more capsules with that substance. In an alternative embodiment, the aerosol precursor substance may be located in the container 1602 (e.g. in a flexible bladder) while capsules may be used for flavoring of that substance or to provide ingredients other than flavoring agents, such as nicotine. In particular, the capsule may act as a supplement to the aerosol precursor substance which may be present in a separate fluid container from the capsule. In an alternative embodiment, the capsule may be in a fluid container that includes the aerosol precursor substance and they are mixed upon activation of the capsule. The fluid container may be a flexible bladder as discussed above.

The overall shape of a capsule can vary. Typically, representative capsules are generally spherical in shape. However, the outer shell of the capsule can be adapted to have shapes that can be characterized as being, for example, generally cylindrical, bean-shaped, ovaloid or elongated in nature. FIG. 17 illustrates alternative embodiments of capsules. The capsules 1603 in FIG. 16 are merely exemplary and may be in different shapes. FIG. 17 illustrates capsules of different shapes. In addition, the capsules may be different sizes. There may be a single large capsule or many smaller microcapsules. FIG. 17 illustrates a tubular capsule 1702, a square capsule 1704, an oval or egg shaped capsule 1706, or a round/circular/spherical capsule 1708. The shapes shown in FIG. 17 are merely exemplary. Activation of those capsules may be similar to or the same as the capsules 1603 in FIG. 16.

The size of the capsule can vary. For example, a relatively large sized capsule that employed to replace the collapsible bladder, the capsule can have an overall size that in comparable to that of the previously described collapsible bladder. The capsule also can be relatively small; and as such, for example, a plurality of microcapsules (e.g., about 50 to about 200 of such small capsules) can be incorporated within each aerosol delivery device. Additionally, spherical capsules having diameters of about 0.5 mm to about 3 mm can be incorporated within each aerosol delivery device; and in such a circumstance, an exemplary aerosol delivery device can incorporate 1 such capsule to about 10 capsules.

FIG. 18 illustrates an alternative cartridge 1800 for an aerosol delivery device including one or capsules disposed adjacent the heating element. In particular, the cartridge 1800 illustrates that the one or more capsules 1803 may be disposed or located adjacent the heating element 1814. The heating element 1814 may include a wick and heater. The wick receives the aerosol precursor substance or other fluid from activation of the capsules 1803. Based on the proximity with the capsules 1803 the heating element 1814 may result in the melting of the capsules 1803 or a portion of the capsules 1803. In other words, activation of the capsules 1803 may be through melting from the heating element 1814. A flow-tube 1812 or terminal support may be support the heating element 1814 so that the capsules 1803 are contained and located adjacent the heating element 1814.

FIG. 19 illustrates a breaking mechanism for the capsules. In particular, there may be a moveable element 1902 (similar to the embodiment for opening the elastomeric valve discussed above) which breaks or activates the capsules 1903. As described in the embodiment with an elastomeric valve which is activated for generating a fluid flow path, the capsules 1903 may be activated by being broken or crushed (e.g. microcapsules) by the breaking mechanism. The capsules 1903 may be broken by a force or stress applied by a user with the moveable element 1902 upon usage of the device. The force may include compressive force applied to the exterior or shell (i.e., a mechanical force such as squeezing or twisting) to rupture and release the substance in the capsules 1903.

In an alternative embodiment, the capsule(s) 1903 may be located adjacent the moveable element 1902. The direct force from the moveable element 1902 may cause breakage of the capsule(s) 1903. In an embodiment similar to that shown in FIG. 18, the capsule(s) 1903 may be adjacent the heating element.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in the Figures or as otherwise described above may be included in an aerosol delivery device according to the present disclosure.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

It is intended that the foregoing detailed description be understood as an illustration of selected forms that the invention can take and not as a definition of the invention. It is only the following claims, including all equivalents that are intended to define the scope of the claimed invention. Finally, it should be noted that any aspect of any of the preferred embodiments described herein can be used alone or in combination with one another.

We claim:

1. An electronic cigarette comprising:
   a battery portion; and
   a cartridge that receives power from the battery portion and stores a fluid that is vaporized, the cartridge comprising:
   an external tube;
   a flexible bladder holding the fluid;
   a tube supporting the flexible bladder that is located inside the external tube, wherein air flows between the external tube and the tube supporting the flexible bladder; and
   a cap that seals the flexible bladder, wherein the cap includes a porous material for transporting the fluid from the bladder.

2. The device of claim 1 wherein the flexible bladder equalizes a pressure inside the flexible bladder to control leakage caused by pressure changes, wherein the equalization of pressure is due to a shape of the flexible bladder collapsing as the fluid is removed.

3. The device of claim 1 wherein the vaporization is caused by a heating of the fluid.

4. The device of claim 3 wherein the cartridge comprises:
   a wick that receives the fluid; and
   a heating element that heats the fluid on the wick to cause the vaporization.

5. The device of claim 4 wherein the heating element comprises a coil that is wrapped around the wick.

6. The device of claim 4 wherein the wick is coupled with the cap of the cartridge for receiving a fluid transfer.

7. The device of claim 6 wherein the porous material comprises a porous ceramic, and the fluid transfer comprises a slow weeping of the fluid from the porous ceramic of the cap onto the wick.

8. The device of claim 4 wherein the heating element receives the power form the battery portion for heating and vaporizing the fluid.

9. The device of claim 1 wherein the cap seals the flexible bladder by creating a compression fit of the flexible bladder with the tube.

10. The device of claim 1 wherein the tube comprises a bladder support cylinder and an exterior of the cartridge is defined by the external tube.

11. The device of claim 1 wherein the cartridge comprises a mouthpiece at one end of the external tube.

12. The device of claim 1 wherein the cartridge is disposable and can be replaced with a new cartridge when the flexible bladder is empty of the fluid.

13. A cartridge assembly for an aerosol delivery device comprising:
    a flexible bladder comprising a thin plastic or latex bag that stores an aerosol precursor substance, wherein the bag adjusts in size as the aerosol precursor substance is used;
    a supporting tube that holds the flexible bladder; and
    a plug at one end of the supporting tube that seals the flexible bladder to control leakage except for a porous portion of the plug that allows the aerosol precursor substance through.

14. The cartridge assembly of claim 13 further comprising:
    an elastomeric seal that results in a compression fit between the plug and the flexible bladder.

15. The cartridge assembly of claim 14 wherein the elastomeric seal comprises a silicone seal, further wherein the supporting tube is open ended and the plug seals one end of the supporting tube using the silicone seal.

16. The cartridge assembly of claim 13 further comprising:
    a heating element that heats the aerosol precursor substance to produce an aerosol, wherein the porous portion of the plug allows for a transportation of the aerosol precursor substance to the heating element.

17. The cartridge assembly of claim 13 further comprising:
    an elastomeric valve that prevents leakage from the porous portion until activation of the elastomeric valve, which enables a path for flow of the aerosol precursor substance, wherein activation comprises receiving a press from a user.

18. The cartridge assembly of claim 13 wherein the adjustments of a size of the bag equalizes pressure within the cartridge to control leakage.

19. A vaporization device comprising:
    a mouthpiece for receiving air with vapor;
    a soft fluid bladder that stores a fluid and prevents excess air in the bladder by collapsing as the fluid is removed;
    a support cylinder that supports the soft fluid bladder;
    a porous material cap that is disposed on one end of the support cylinder and coupled with the soft fluid bladder for leaking a controlled amount of the fluid; and
    an atomizer that generates the vapor from the fluid stored in the soft fluid bladder.

20. The vaporization device of claim 19 wherein the soft fluid bladder comprises a latex or thin plastic and the porous material cap comprises a porous ceramic material.

21. An aerosol delivery device comprising:
    one or more capsules containing an aerosol precursor substance;
    a mechanism for releasing the aerosol precursor substance by breaking the one or more capsules to release the aerosol precursor substance; and
    a vaporizer that receives the aerosol precursor substance after the releasing and generates an aerosol by vaporizing the aerosol precursor substance.

22. The aerosol delivery device of claim 21 wherein the mechanism comprises a moveable portion for the breaking of the one or more capsules.

23. The aerosol delivery device of claim 21 further comprising:
    a wick for transporting the released aerosol precursor substance; and a heating element adjacent the wick for heating the released aerosol precursor substance as part of the vaporizing.

24. The aerosol delivery device of claim 23 wherein the mechanism comprises the heating element for melting at least a portion of the one or more capsules.

25. The aerosol delivery device of claim 23 wherein the capsules are stored and released near the heating element and the wick.

* * * * *